(12) United States Patent
Bandyopadhyay et al.

(10) Patent No.: US 10,743,819 B2
(45) Date of Patent: Aug. 18, 2020

(54) SYSTEM AND METHOD FOR DETERMINING INFORMATION AND OUTLIERS FROM SENSOR DATA

(71) Applicant: Tata Consultancy Serives Limited, Mumbai (IN)

(72) Inventors: Soma Bandyopadhyay, Kolkata (IN); Arpan Pal, Kolkata (IN); Arijit Ukil, Kolkata (IN); Tulika Bose, Kolkata (IN); Chetanya Puri, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 111 days.

(21) Appl. No.: 15/208,230

(22) Filed: Jul. 12, 2016

(65) Prior Publication Data
US 2017/0055913 A1    Mar. 2, 2017

(30) Foreign Application Priority Data
Aug. 27, 2015 (IN) .......................... 3287/MUM/2015

(51) Int. Cl.
*A61B 5/00* (2006.01)
*G06K 9/62* (2006.01)
(Continued)

(52) U.S. Cl.
CPC .......... *A61B 5/7221* (2013.01); *A61B 5/0002* (2013.01); *A61B 5/02416* (2013.01);
(Continued)

(58) Field of Classification Search
CPC . A61B 5/7221; A61B 5/0002; A61B 5/02416; A61B 5/0402; A61B 5/0476;
(Continued)

(56) References Cited

U.S. PATENT DOCUMENTS

| 7,904,279 B2 | 3/2011 | Miguelanez et al. |
| 8,006,157 B2 | 8/2011 | Abe et al. |

(Continued)

OTHER PUBLICATIONS

Zhao, A simple and effective outlier detection algorithm for categorical data, Springer/Researchgate, Int. J. Mach. Learn. & Cyber. (2014) 5:469-477 (Year: 2013).*

(Continued)

*Primary Examiner* — Lisa E Peters
(74) *Attorney, Agent, or Firm* — Finnegan, Henderson, Farabow, Garrett & Dunner LLP

(57) ABSTRACT

The present subject matter discloses a system and a method for identifying information from sensor data in a sensor agnostic manner. The system may receive sensor data provided by a sensor and may determine statistical features of the sensor data. The system may determine signal dynamics of the sensor data based on at least one of the statistical features, signal processing features, and a data distribution model. The system may select at least one outlier class based on the signal dynamics, number of streams of the sensor data, and dimensions of the sensor data. The system may select at least one outlier detection method associated with an outlier class for detecting outliers in the sensor data. The system may determine information content of the sensor data based on the outliers, the signal dynamics, the statistical features, and information theoretic features, and similarity or dissimilarity measure.

14 Claims, 2 Drawing Sheets

(51) Int. Cl.
  *A61B 5/024*    (2006.01)
  *A61B 5/0402*   (2006.01)
  *A61B 5/0476*   (2006.01)
(52) U.S. Cl.
  CPC .......... *A61B 5/0402* (2013.01); *A61B 5/0476* (2013.01); *A61B 5/7203* (2013.01); *A61B 5/7246* (2013.01); *A61B 5/7257* (2013.01); *A61B 5/7264* (2013.01); *G06K 9/6284* (2013.01)
(58) Field of Classification Search
  CPC ... A61B 5/7203; A61B 5/7246; A61B 5/7257; A61B 5/7264
  See application file for complete search history.

(56) References Cited

U.S. PATENT DOCUMENTS

| | | | |
|---|---|---|---|
| 8,140,301 B2 | 3/2012 | Abe et al. | |
| 8,620,729 B2* | 12/2013 | Srinivasa | G06Q 10/04 705/7.37 |
| 2003/0061015 A1* | 3/2003 | Ben-Gal | G06K 9/6282 703/2 |
| 2007/0191688 A1* | 8/2007 | Lynn | A61B 5/412 600/300 |
| 2008/0091118 A1* | 4/2008 | Georgopoulos | A61B 5/04008 600/544 |
| 2010/0211594 A1 | 8/2010 | Penders et al. | |
| 2010/0292545 A1* | 11/2010 | Berka | A61B 5/048 600/301 |
| 2012/0101401 A1* | 4/2012 | Faul | A61B 5/0476 600/544 |
| 2012/0123232 A1* | 5/2012 | Najarian | A61B 5/0022 600/345 |
| 2014/0039274 A1* | 2/2014 | Sarrafzadeh | A61B 5/1118 600/300 |
| 2014/0074796 A1* | 3/2014 | Akoglu | H04L 63/1425 707/687 |
| 2014/0142443 A1* | 5/2014 | Ngo | A61B 5/0006 600/486 |
| 2015/0031965 A1* | 1/2015 | Visvanathan | A61B 5/0059 600/301 |
| 2015/0133795 A1* | 5/2015 | Tomaselli | A61B 5/0452 600/484 |
| 2015/0164428 A1* | 6/2015 | Townsend | A61B 5/7221 702/69 |
| 2015/0199010 A1* | 7/2015 | Coleman | A61B 5/0006 345/156 |
| 2016/0174926 A1* | 6/2016 | Londt | A61B 6/5288 378/8 |
| 2017/0315531 A1* | 11/2017 | Aparicio Ojea | G05B 19/05 |

OTHER PUBLICATIONS

Chandola et al, Anomaly Detection:A Survey, ACM Computing Surveys, 09, 2009, pp. 1-72 (Year: 2009).*

* cited by examiner

SYSTEM AND METHOD FOR DETERMINING INFORMATION AND OUTLIERS FROM SENSOR DATA

PRIORITY CLAIM

This U.S. patent application claims priority under 35 U.S.C. § 119 to: India Application No. 3287/MUM/2015, filed on Aug. 27, 2015. The entire contents of the aforementioned application are incorporated herein by reference.

TECHNICAL FIELD

This disclosure relates generally to sensor data analysis for outlier detection, and more particularly to system and method for determining information and outliers from sensor data.

BACKGROUND

Sensors are used across different applications to capture information. Sensor data captured by the sensor may comprise various types of information. The information may either be sensitive, non-sensitive or context information. The sensor data may be processed for determining outliers related to the sensor data. The outliers may indicate critical information present in the sensor data.

For an example, outliers of Electrocardiogram (ECG) data may indicate abnormal pattern related to heart activity and may thus indicate a heart disease. The outliers of ECG data may be analyzed to determine criticality of a heart condition. Thus, critical data and non-critical data of ECG of a patient may be transmitted with different reliability, information update rate and priority level with reduced communication cost and energy.

Different sensors are used for analyzing different kinds of activity and different data processing techniques are used based on the type of data. Further, different outlier detection techniques are used based on features of the sensor data. Thus, it is always required to know about the signal dynamics of sensor data to be processed in order to derive information out of the sensor data as well as derive anomaly and use it further.

SUMMARY

Embodiments of the present disclosure present technological Improvements as solutions to one or more of the above-mentioned technical problems recognized by the inventors in conventional systems. This summary is provided to introduce aspects related to identifying information from sensor data and the aspects are further described below in the detailed description. This summary is not intended to identify essential features of the claimed subject matter nor is it intended for use in determining or limiting the scope of the claimed subject matter.

In one implementation, a method for identifying information from sensor data is disclosed. The method may comprise receiving sensor data provided by a sensor. The method may also comprise determining signal dynamics of the sensor data based on at least one of the statistical features, signal processing features, and a data distribution model. The method may comprise selecting at least one outlier class based on the signal dynamics, number of streams of the sensor data, and dimensions of the sensor data. The outlier class may be at least one of point detection, collaborative, and contextual. The method may further comprise selecting at least one outlier detection method associated with an outlier class for detecting outliers in the sensor data. The at least one outlier detection method may belong to the at least one outlier class. The method may comprise determining information content of the sensor data based on the outliers, the signal dynamics, the statistical features, and information theoretic features. The method may further comprise determining an information score corresponding to each outlier, based on the signal dynamics, the outlier class, and the information content, wherein the information score is indicative of amount of information associated with each outlier. The method may further comprise identifying one or more outliers with highest information content based on the information score.

In one implementation, a system for identifying information from sensor data is disclosed. The system comprises a memory coupled to a processor for executing programmed instructions stored in the memory. The processor may receive sensor data provided by a sensor. The processor may further determine signal dynamics of the sensor data based on at least one of the statistical features, signal processing features, and a data distribution model. The processor may select at least one outlier class based on the signal dynamics, number of streams of the sensor data, and dimensions of the sensor data. The outlier class may be at least one of point detection, collaborative, and contextual. The processor may select at least one outlier detection method for detecting outliers in the sensor data. The at least one outlier detection method may belong to the at least one outlier class. The processor may determine information content of the sensor data based on the outliers, the signal dynamics, the statistical features, and information theoretic features. The processor may determine an information score corresponding to each outlier, based on the signal dynamics, the outlier class, and the information content, wherein the information score is indicative of amount of information associated with each outlier. The processor may identify one or more outliers with highest information content based on the information score.

In one implementation, a non-transitory computer readable medium embodying a program executable in a computing device for identifying information from sensor data is disclosed. The program may comprise a program code for receiving sensor data provided by a sensor. The program may comprise a program code for determining signal dynamics of the sensor data based on at least one of the statistical features, signal processing features, and a data distribution model. The program may comprise a program code for selecting at least one outlier class based on the signal dynamics, number of streams of the sensor data, and dimensions of the sensor data. The outlier class may be at least one of point detection, collaborative, and contextual. The program may comprise a program code for selecting at least one outlier detection method for detecting outliers in the sensor data. The at least one outlier detection method may belong to the at least one outlier class. The program may comprise a program code for determining information content of the sensor data based on the outliers, the signal dynamics, the statistical features, and information theoretic features. The processor may comprise a program code for determining an information score corresponding to each outlier, based on the signal dynamics, the outlier class, and the information content, wherein the information score is indicative of amount of information associated with each outlier. The processor may comprise a program code for identifying one or more outliers with highest information content based on the information score.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Systems and methods for identifying information from sensor data are described. The system may receive sensor data provided by a sensor. Further, the system may determine statistical features of the sensor data like central tendency, dispersion, etc. The system may determine signal dynamics of the sensor data based on at least one of the statistical features, signal processing features, and a data distribution model. In one embodiment, signal processing methods like Discrete Fourier Transform (DFT), Fast Fourier Transform (FFT), Inverse Fast Fourier Transform (IFFT), and auto-correlation, various shape descriptors like Skewness, Kurtosis can be used for determining signal dynamics of the sensor data.

Post determining the signal dynamics, the system may select at least one outlier class based on the signal dynamics, number of streams of the sensor data, and dimensions of the sensor data. In one case, the outlier class may be at least one of point detection, collaborative, and contextual. Subsequently, the system may select at least one outlier detection method for detecting outliers in the sensor data. The at least one outlier detection method may belong to the at least one outlier class. The system may determine information content of the sensor data based on the outliers, the signal dynamics, the statistical features, and information theoretic features.

While aspects of described system and method for identifying information from sensor data may be implemented in any number of systems, different computing systems, environments, and/or configurations, the embodiments are described in the context of the following exemplary system.

Figure 1:
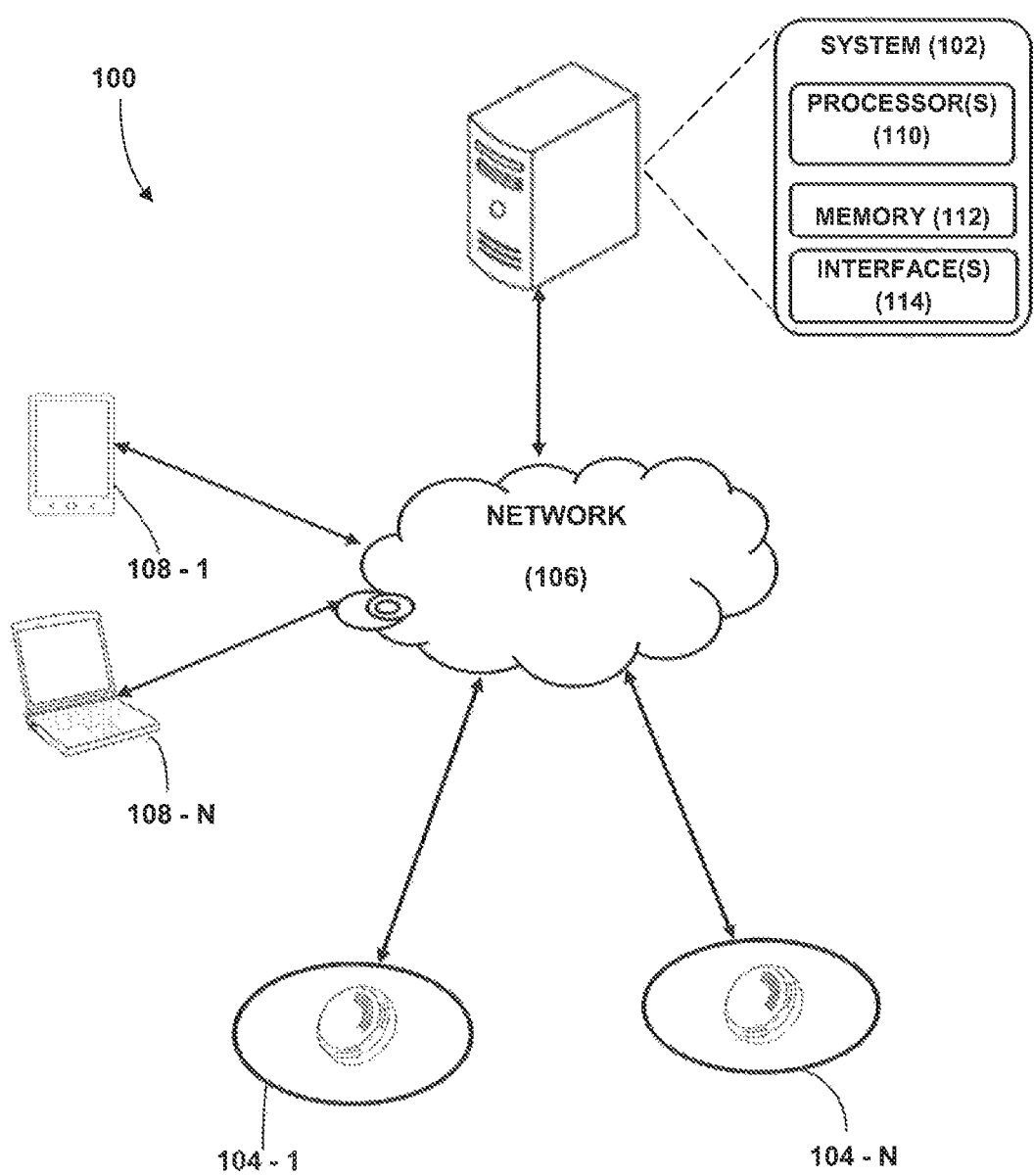
FIG. 1 illustrates a network implementation of a system for identifying information from sensor data, in accordance with an embodiment of the present subject matter.

Referring now to FIG. 1, a network implementation 100 of a system for identifying information from sensor data is shown, in accordance with an embodiment of the present subject matter. Although the present subject matter is explained considering that the system 102 is implemented on a computer, it may be understood that the system 102 may also be implemented in a variety of computing systems including but not limited to, a smart phone, a tablet, a notepad, a personal digital assistant, a handheld device, a laptop computer, a notebook, a workstation, a mainframe computer, a server, and a network server. In one embodiment, the system 102 may be implemented in a cloud-based environment. It will be understood that the system 102 may be accessed by multiple users through one or more user devices 108-1 . . . 108-N, collectively referred to as user device 108 hereinafter, or applications residing on the user device 108. Examples of the user device 108 may include, but are not limited to, a portable computer with a webcam, a personal digital assistant with a camera, a handheld device with a camera, and a digital camera. The user device 108 is communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. Further the network 106 may include a variety of network devices, including routers, bridges, servers, computing devices, storage devices, and the like.

In one embodiment, as illustrated using the FIG. 1, the system 102 may include at least one processor 110, a memory 112, and input/output (I/O) interfaces 114. Further, the at least one processor 110 may be implemented as one or more microprocessors, microcomputers, microcontrollers, digital signal processors, central processing units, state machines, logic circuitries, and/or any devices that manipulate signals based on operational instructions. Among other capabilities, the at least one processor 110 is configured to fetch and execute computer-readable instructions stored in the memory 112.

The I/O interfaces 114 may include a variety of software and hardware interfaces, for example, a web interface, a graphical user interface, and the like. The I/O interfaces 114 may allow the system 102 to interact with a user directly. Further, the I/O interfaces 114 may enable the system 102 to communicate with other computing devices, such as web servers and external data servers (not shown). The I/O interfaces 114 can facilitate multiple communications within a wide variety of networks and protocol types, including wired networks, for example, LAN, cable, etc., and wireless networks, such as WLAN, cellular, or satellite.

The memory 112 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Further, referring to the FIG. 1, functioning of the system 102 for identifying information from sensor data is explained henceforth. Sensors (104-1 to 104-N) may be placed across remote locations to capture sensor data. The sensors 104 may be a part of Internet of Things (IoT), wherein the sensors 104 are connected using Wireless Sensor Network (WSN) or any other relevant communication channel. In one case, the sensors 104 may be used to capture different categories of data. In one case, the different categories of data may include periodic data, random data, and non-stationary data. The periodic data may include Electrocardiogram (ECG) data and Photoplethysmogram (PPG) data. The random data may include Electroencephalogram (EEG) data and smart meter data. The non-stationary data may comprise the smart meter data, the EEG data, stock data, and accelerometer data. Further, the sensor data captured by the sensor 104 may be transmitted to the system 102 via the network.

Upon receiving the sensor data, the system 102 may apply data processing techniques on the sensor data. In one case, the data processing techniques may comprise Discrete Fourier Transform (DFT), Fast Fourier Transform (FFT), Inverse Fast Fourier Transform (IFFT), auto-correlation, and the like. Upon applying the data processing techniques, the system 102 may determine statistical features of the sensor data. In one case, the statistical features may comprise at least one of mean value, standard deviation, kurtosis, dispersion, variance, covariance, auto-covariance, correlation, and auto-correlation.

Based on the statistical features, the system 102 may determine signal dynamics of the sensor data. In one case, the system 102 may also use signal processing features such as periodicity and a data distribution parameter such as Autoregressive Moving Average (ARMA), ARIMA based models' values along with statistical parameters such as mean, median, kurtosis in order to determine the signal dynamics. Further, the system 102 may use the statistical features, the signal processing features, and the data distribution model in a hierarchical manner i.e. utilize them in a sequence for determining the signal dynamics.

Post determining the signal dynamics, the system 102 may select at least one outlier class based on the signal dynamics. In addition, the system 102 may also utilize a number of streams of the sensor data, and dimensions of the sensor data along with the signal dynamics for selecting the at least one outlier class. In one case, an outlier class may be at least one of point detection, collaborative, and contextual. The point detection outlier class may either be distance based or density based. The collaborative outlier class may be related to clustering or a sub-sequence match. The collaborative outlier detection techniques are configured to consider a certain contiguous set of points instead of just comparing a single point, where a certain portion of a time series/signal is known as sub-sequence. One technique of outlier detection could be comparing several such sub-sequences from a given time series and finding the most unusual sub-sequence. Below mentioned is an example explaining about selecting the outlier class.

In one case, the sensor data may be identified as $S\beta$ having a sample size N. $S\beta$ {S} may indicate a univariate sensor data and $\{S\beta_1 \ldots S\beta_r\}$ may indicate a multivariate sensor data having multiple data sequences. The system 102 may determine a subsequence length as, $$s1 = N/n \qquad \text{Equation 1}$$

Here, in the Equation 1, n indicates number of subsequences. The system 102 may determine the statistical features of the sensor data. In one case, the system may determine a central tendency and dispersion of the subsequence as the statistical features. While the central tendency and the dispersion of the subsequence remains same for a period of time, the sensor data may be identified as stationary. Else, the sensor data may be identified as non-stationary when the central tendency and the dispersion of sensor data changes after a period of time. Further, the system 102 may confirm the stationary or non-stationary nature of the sensor data using the data model. In one case, the system 102 may use an ARIMA model to conform the nature of the sensor data. In this case, the system 102 may select the outlier class as contextual.

In another case, the system 102 may consider a lag of T. The system 102 may perform a data processing technique like autocorrelation between sensor data $S\beta_t$ and $S\beta_{k+t}$, and DFT on the sensor data $S\beta$, as mentioned below.

$$\text{acor}(S\beta_t, S\beta_{k+t}); \text{DFT}(S\beta) \rightarrow am; t:1 \text{ to } N; k=k+\tau$$

The system 102 may perform a periodic check of the value am[k] using the above auto correlation equation in a periodic manner. While periodic high amplitude is obtained during the periodic check, the system 102 may select the outlier class as collaborative.

In yet another case, the system 102 may determine kurtosis and skewness of the sensor data $S\beta$. While a leptokurtic and skewed pattern is obtained, the system 102 may select the outlier class as contextual.

Post selection of the at least one outlier class, the system 102 may select at least one outlier detection method for detecting outliers in the sensor data. The at least one outlier detection method may belong to the at least one outlier class. Subsequently, the system 102 may determine information content of the sensor data based on the outliers, the signal dynamics, the statistical features, and information theoretic features. The information theoretic features may indicate variation of information and entropy. The information content may be measured in terms of distances, code lengths, entropies, distances based on mutual information, dynamic time warping, as measure of similarity or dissimilarity, and estimation errors. The distances may be represented using at least one category selected from a group consisting of k-nearest neighbor distance, distance to closest cluster centroids, local density value, Euclidean distance, and Mahalanobis (ML) distance.

In one embodiment, the system 102 may validate the outliers and the information content based on the signal dynamics. In one case, the outliers may be validated using adaptive data compression technique and adaptive data dissemination technique. In other words, the part of the data signals without any outliers/information are compressed more whereas the part of the data signal with outliers compressed less, by this adaptive compression over all information loss is less. In case of adaptive data dissemination technique, signals without outliers/information may be disseminated with lower priority.

In another embodiment, the system 102 may determine an information score based on the signal dynamics, the outlier class, and the information content. The information score may be a parameter indicative of amount of information including a measure of similarity or dissimilarity score like variation of information based on mutual information or Dynamic Time Warping (DTW). Further, the system 102 may identify outliers having high information content.

In yet another embodiment, the system 102 may normalize the information score by removing outlier errors. In order to remove the outlier errors, the system 102 may perform a series of steps as explained henceforth. Initially, the system 102 may determine precision (p). The precision may indicate a percentage of relevant outliers determined by the system 102. In one case, the precision may be determined using a below mentioned Equation 2.

$$\text{Precision}(p) \triangleq \frac{TP}{TP + FP} \qquad \text{Equation 2}$$

In the Equation 2, TP indicates True positives i.e. true outliers detected by the system 102. FP indicates False positives i.e. outliers that are detected by the system 102 but are not true outliers. Further, the system 102 may determine recall (r). The recall may also be identified as a True Positive Rate (TPR) and may indicate a percentage of relevant outliers determined by the system 102. In one case, the recall may be determined using a below mentioned Equation 3.

$$\text{Recall}(r) \triangleq \frac{TP}{TP+FN} \qquad \text{Equation 3}$$

In the Equation 3, TP denotes the True positives. FN denotes False Negatives i.e. true outliers not detected by the system 102. Post determining the precision (p) and the recall (r), the system 102 may determine a $F_1$ score. In one case, the $F_1$ score may be determined using a below mentioned Equation 4.

$$F_1 \text{Score} \triangleq \frac{2pr}{p+r} \qquad \text{Equation 4}$$

Successively, the system 102 may determine a False Positive Rate (FPR) using a below mentioned Equation 5.

$$FPR = 1 - \text{Specificity} = \frac{FP}{FP+TN} \qquad \text{Equation 5}$$

In the Equation 5, FP denotes the False Positives. TN denotes True Negatives i.e. data values not detected by the system 102 and are not outliers. Specificity indicates a proportion of negatives correctly identified by the system 102:

In one embodiment, the system 102 may generate a Receiver Operating Characteristic (ROC) curve. The ROC curve may be created between the True Positive Rate (TPR) and the False Positive Rate (FPR). The ROC curve may show a tradeoff between the 'sensitivity' and '1-specificity'. Each predicted result may denote one point in the ROC space. The ROC space is plotted as a curve by varying threshold of a binary classifier, which varies the number of true positives and false negatives, and then Area Under the Curve (AUC) can be used to quantify the accuracy of the classifier.

In one case, the system 102 may select different values of parameters for determining an optimum or a least value of the False Positive Rate (FPR) without affecting the True Positive Rate (TPR). In an example, the system 102 may use (in an exemplary case) DB-SCAN clustering based outlier detection method. A distance threshold parameter may be set as 'τ' and minpts may be set as '∈.' The minpts is the minimum number of points to lie inside the spherical boundary of diameter given by 'τ' (also known as distance threshold) to consider the point as a core-point. Further, the system 102 may obtain a significant number of False Positives (FP), at a particular detection rate. Thus, to reduce the significant number of False Positives (FP), the system 102 may use the DB-SCAN technique using different values of the distance threshold parameter and the minpts, without affecting the True Positive Rate (TPR). The system 102 may thus adapt in an above explained manner to reduce the number of False Positives (FP).

Thus, in one embodiment, the system 102 may identify information from sensor data in the above described manner. It must be understood that the system 102 may identify information from sensor data in other manners lying within the spirit and scope of the present subject matter.

Figure 2:
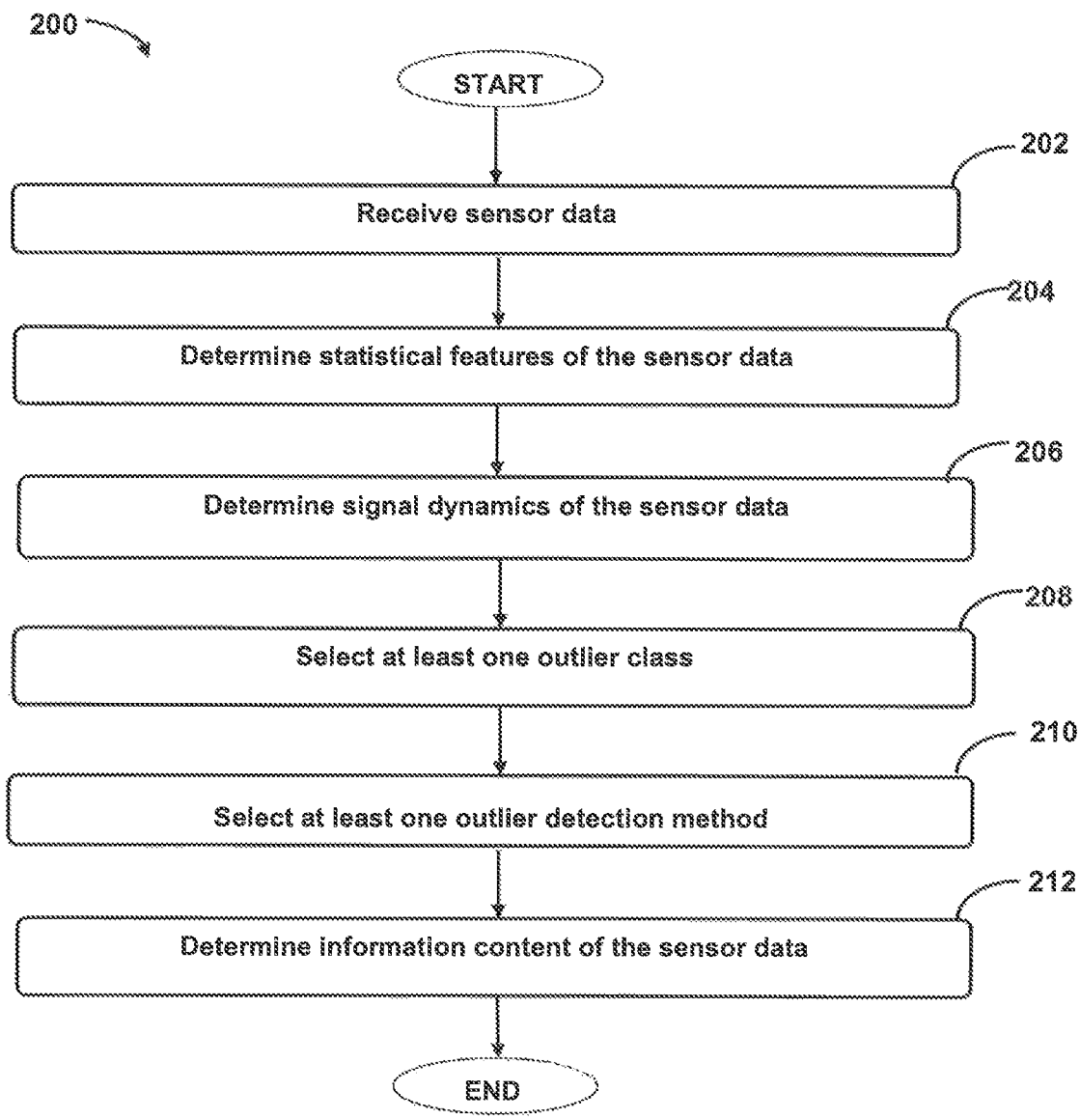
FIG. 2 shows a flowchart illustrating a method for identifying information from sensor data, in accordance with an embodiment of the present subject matter.

Referring now to FIG. 2, a flowchart 200 illustrating a method for identifying information from sensor data is described in accordance with an embodiment of the present subject matter. The method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communications network. In a distributed computing environment, computer executable instructions may be located in both local and remote computer storage media, including memory storage devices.

The order in which the method 200, as illustrated in FIG. 2, is described is not intended to be construed as a limitation, and any number of the described method blocks can be combined in any order to implement the method 200 or alternate methods. Additionally, individual blocks may be deleted from the method 200 without departing from the spirit and scope of the subject matter described herein. Furthermore, the method can be implemented in any suitable hardware, software, firmware, or combination thereof. However, for ease of explanation, in the embodiments described below, the method 200 may be considered to be implemented on the above described system 102.

At block 202, sensor data provided by a sensor may be received. The sensor data may be received by the system 102.

At block 204, statistical features of the sensor data may be determined from the sensor data. The statistical features may comprise at least one of a mean value, standard deviation, kurtosis, dispersion, variance, covariance, auto-covariance, correlation, and auto-correlation. The statistical features of the sensor data may be determined by the system 102 using frequency analysis techniques such as DFT, FFT, IFFT, or auto-correction technique.

At block 206, the signal dynamics of the sensor data may be determined based on at least one of the statistical features, signal processing features, and a data distribution model. The signal dynamics is dependent of the type of sensors used for capturing the signal data. The signal dynamics may be at least one of stationary, non-stationary, random, non-random, periodic, quasi-periodic, and non-periodic. The signal dynamics of the sensor data may be determined by the system 102.

At block 208, at least one outlier class may be selected based on the signal dynamics, number of streams of the sensor data, and dimensions of the sensor data. The outlier class may be at least one of point detection, collaborative, and contextual. The at least one outlier class may be selected by the system 102.

At block 210, at least one outlier detection method corresponding to the identified outlier class may be selected for detecting outliers in the sensor data. The at least one outlier detection method may belong to the at least one outlier class. The at least one outlier detection method may be selected by the system 102. For example, the system 102 may suggest using probabilistic modeling in case if information score is to be determined by likelihood fit of a data point. Further, the system 102 may suggest using linear modeling in case of residual distance of data points to the lower dimensional representation of the data.

At block 212, information content of the sensor data may be determined. The Information content may be determined based on the outliers, the signal dynamics, the statistical features, and information theoretic features. The information content may be measured in terms of distances, code lengths, entropies, distances based on mutual information, dynamic time warping, as measure of similarity or dissimilarity, and estimation errors. The information content of the sensor data may be determined by the system 102. In one embodiment, the system 102 may determine an information score based on the signal dynamics, the outlier class, and the Information content. The information score may be determined by likelihood fit of a data point in case of probabilistic modeling. Further, in case of proximity based modeling, the distance measures such as distance to closest cluster centroids, or local distance grounds, or Euclidian distance may be considered for generating the information score. Further, in case of linear modeling, residual distance of data points to the lower dimensional representation of the data may be considered. Furthermore, in case of temporal modeling, deviation from a forecasted/predicted value may be considered. In a similar manner, any other techniques and corresponding measures may be used for determining the information score. The information score may be a parameter indicative of amount of information.

Further, the system 102 may identify outliers having high information content. Based on the identified outliers, the system 102 may normalize the information score by removing outlier errors. In order to remove the outlier errors, the system 102 may perform a series of steps as explained in the following algorithm.

order to identify and rank the outliers. For example if an outlier class is determined as Collaborative, in the next step clustering algorithms such as k-Means or DB-SCAN may be used followed by point based or Contextual analysis as per derived $S\delta$. Further, the information content of the outliers are derived as described in block 212, part sensor data without any valid outliers and showing lower information score may be compressed more whereas, the parts of sensor data which have valid outliers with higher information value may be left uncompressed for further analysis and reporting.

Although implementations for methods and systems for identifying information from sensor data have been described in language specific to structural features and/or methods, it is to be understood that the appended claims are not necessarily limited to the specific features or methods described. Rather, the specific features and methods are disclosed as examples of Implementations for identifying information from sensor data.

Exemplary embodiments discussed above may provide certain advantages. Though not required to practice aspects of the disclosure, these advantages may include those provided by the following features.

Some embodiments may enable a system and a method to determine information form sensor data in a sensor agnostic manner.

Some embodiments may enable a system and a method to remove errors or false detection of outliers.

Some embodiments may enable a system and a method to adapt so as to reduce a number of False Positives (FP) in the outlier detection technique.

```
Initially the system accepts Sensor Data Sβ {S} (univariate) or
{Sβ₁ ... .Sβᵣ} (muitivariate/multiple), sample size (N):   Subsequence length sl = N/n,
number of subsequences: n, and Lag: τ.
For {Sβ₁ to Sβᵢ} where {i= 1 to r; (i = 1 indicates presence of single data stream i.e.,
Univariate: Sβ)}
    Loop j = 1:n
        Determine central tendency→fc(sl); dispersion→ fd(sl)
            if j > 2
                    if ( (fc(sl)ⱼ₋₁ == fc(sl)ⱼ ) and (fd(sl)ⱼ₋₁ = =        fd(sl)ⱼ )→Sδ =
Stationary→ARMA(p,q)
                else Sδ = Non-stationary; confirmation by fitting into ARIMA   (p,d,q) model;
                endif
            endif
        Endloop
        Loop from k = 1: (N/τ)
            Determine autocorrelation and DFT→cor(Sβₜ, Sβₖ₊ₜ);
            DFT(Sβ) → am; t=1:N ;
            k = k +τ,
            if Periodicity_check(am[k]) gives periodic high        amplitude → Sδ = Periodic;
            Endif
        Endloop
        Sβ →Kurtosis and Skewness→shows leptokurtic,
        skewed→ Sδ =non_stationary_random
        Endloop
Endfor
if { Sβ} Univariate
    if (Sδ == Stationary)
    → Outlier class: Point based outlier, Contextual
    eiseif (Sδ == Nonstationary)
    → Outlier class: Point based outlier, Contextual
    elseif (Sδ == Periodic)
    → Outlier class: Collaborative
    elseif (Sδ == non stationary random)
    → Outlier class: Point based outlier
endif
else {Sβ₁ ... .Sβᵣ} : Multivariate/ Multiple streams:
```

Based on the above algorithm, a hierarchical approach is adapted to determine the outlier class. Based on the outlier class determined, the system analyzes the sensor data in The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in Implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for determining information from sensor data, the method comprising:
    receiving, by a processor, sensor data provided by a sensor, wherein the sensor data comprise periodic data, random data, or non-stationary data, wherein the periodic data include Electrocardiogram (ECG) data and Photoplethysmogram (PPG) data, wherein the random data include Electroencephalogram (EEG) data and smart meter data and wherein the non-stationary data include the smart meter data, the EEG data, stock data, and accelerometer data;
    determining, by the processor, statistical features of the sensor data using data processing techniques;
    determining, by the processor, signal dynamics of the sensor data based on the statistical features, signal processing features, and a data distribution model, wherein the data distribution model comprises Autoregressive Moving Average (ARMA) based model and or AutoRegressive Integrated Moving Average (ARIMA) based model and wherein the signal processing features comprises features associated with periodicity;
    identifying, by the processor, at least one outlier class based on the signal dynamics and number of streams of the sensor data, wherein the outlier class is at least one of point detection, collaborative, or contextual and wherein the point detection outlier class is related to one of a distance parameter or a density parameter;
    selecting, by the processor, at least one outlier detection method for detecting outliers in the sensor data based on the identified at least one outlier class;
    determining, by the processor, information content of the sensor data based on detected outliers, the signal dynamics, the statistical features, and information theoretic features of the sensor data, wherein the information content of the sensor data is a measure of one or more features of the sensor data and is determined using a data modeling technique corresponding to the measure of one or more features of the sensor data and wherein the information theoretic features indicate variation of information and entropy;
    determining, by the processor, an information score for the information content of the sensor data based on the signal dynamics, the identified at least one outlier class, wherein the information score is indicative of amount of information including a measure of similarity or dissimilarity score associated with each outlier;
    normalizing the information score by removing identifying outlier errors, wherein the identifying outlier errors are one of false positives;
    identifying, by the processor, one or more outliers with highest information content based on the information score and
    validating the outliers using adaptive data compression and adaptive dissemination and validating the information content of the sensor data based on the signal dynamics.

2. The method of claim 1, wherein the statistical features comprise one or more of a mean value, standard deviation, kurtosis, dispersion, variance, covariance, auto-covariance, correlation, and auto-correlation.

3. The method of claim 1, wherein the signal dynamics is at least one of stationary, non-stationary, random, non-random, periodic, quasi-periodic, or non-periodic.

4. The method of claim 1, wherein the information content is measured in terms of at least one of distances, code lengths, entropies, distances based on mutual information, dynamic time warping, measure of similarity or dissimilarity or estimation errors.

5. The method of claim 4, wherein the distances are represented using at least one category selected from a group consisting of k-nearest neighbor distance, distance to closest cluster centroids, local density value, Euclidean distance, and Mahalanobis (ML) distance.

6. The method of claim 1, further comprising validating the outliers and the information content based on the signal dynamics, wherein the outliers are validated using adaptive data compression and adaptive data dissemination.

7. The method of claim 1, wherein the outlier errors are determined using precision, recall, and specificity.

8. A system for determining information from sensor data, the system comprises:
    a processor;
    a memory coupled to the processor, wherein the processor is capable of executing programmed instructions stored in the memory to:
        receive sensor data provided by a sensor, wherein the sensor data comprise periodic data, random data, or non-stationary data, wherein the periodic data include Electrocardiogram (ECG) data and Photoplethysmogram (PPG) data, wherein the random data include Electroencephalogram (EEG) data and smart meter data and wherein the non-stationary data include the smart meter data, the EEG data, stock data, and accelerometer data;
determine statistical features of the sensor data using data processing techniques;
determine signal dynamics of the sensor data based on the statistical features, signal processing features, and a data distribution model, wherein the data distribution model comprises Autoregressive Moving Average (ARMA) based model or Autoregressive Integrated Moving Average (ARIMA) based model and wherein the signal processing features comprises features associated with periodicity;
identify at least one outlier class based on the signal dynamics and number of streams of the sensor data, wherein the outlier class is at least one of point detection, collaborative, or contextual and wherein the point detection outlier class is related to one of a distance parameter or a density parameter;
select at least one outlier detection method for detecting outliers in the sensor data based on the identified at least one outlier class;
determine information content of the sensor data based on detected outliers, the signal dynamics, the statistical features, and information theoretic features of the sensor data, wherein the information content of the sensor data is a measure of one or more features of the sensor data and is determined using a data modeling technique corresponding to the measure of one or more features of the sensor data and wherein the information theoretic features indicate variation of information and entropy;
determine an information score for the information content of the sensor data based on the signal dynamics, the identified at least one outlier class, wherein the information score is indicative of amount of information including a measure of similarity or dissimilarity score associated with each outlier;
normalize the information score by removing identifying outlier errors, wherein the identifying outlier errors are one of false positives;
identify one or more outliers with highest information content based on the information score and
validate the outliers using adaptive data compression and adaptive dissemination and validate the information content of the sensor data based on the signal dynamics.

9. The system of claim 8, wherein the statistical features comprise one or more of a mean value, standard deviation, kurtosis, dispersion, variance, covariance, auto-covariance, correlation, and auto-correlation.

10. The system of claim 8, wherein the signal dynamics is at least one of stationary, non-stationary, random, non-random, periodic, quasi-periodic, or non-periodic.

11. The system of claim 8, wherein the information content is measured in terms of at least one of distances, code lengths, entropies, distances based on mutual information, dynamic time warping, measure of similarity or dissimilarity or estimation errors.

12. The system of claim 8, further comprising validating the outliers and the information content based on the signal dynamics, wherein the outliers are validated using adaptive data compression and adaptive data dissemination.

13. The system of claim 8, wherein the outlier errors are determined using precision, recall, and specificity.

14. A non-transitory computer readable medium embodying a program executable in a system for determining information from sensor data, the program comprising:
a program code for receiving sensor data provided by a sensor, wherein the sensor data comprise periodic data, random data, or non-stationary data, wherein the periodic data include Electrocardiogram (ECG) data and Photoplethysmogram (PPG) data, wherein the random data include Electroencephalogram (EEG) data and smart meter data and wherein the non-stationary data include the smart meter data, the EEG data, stock data, and accelerometer data;
a program code for determining statistical features of the sensor data using data processing techniques;
a program code for determining signal dynamics of the sensor data based on the statistical features, signal processing features, and a data distribution model, wherein the data distribution model comprises Autoregressive Moving Average (ARMA) based model and or Autoregressive Integrated Moving Average (ARIMA) based model and wherein the signal processing features comprises features associated with periodicity;
a program code for identifying at least one outlier class based on the signal dynamics and number of streams of the sensor data, wherein the outlier class is at least one of point detection, collaborative, or contextual and wherein the point detection outlier class is related to one of a distance parameter or a density parameter;
a program code for selecting at least one outlier detection method for detecting outliers in the sensor data based on the identified at least one outlier class;
a program code for determining information content of the sensor data based on detected outliers, the signal dynamics, the statistical features, and information theoretic features of the sensor data, wherein the information content of the sensor data is a measure of one or more features of the sensor data and is determined using a data modeling technique corresponding to the measure of one or more features of the sensor data and wherein the information theoretic features indicate variation of information and entropy;
a program code for determining an information score for the information content of the sensor data based on the signal dynamics, the identified at least one outlier class, wherein the information score is indicative of amount of information including a measure of similarity or dissimilarity score associated with each outlier;
a program code for normalizing the information score by removing identifying outlier errors, wherein the identifying outlier errors are one of false positives;
a program code for identifying one or more outliers with highest information content based on the information score and a program code for validating the outliers using adaptive data compression and adaptive dissemination and validating the information content of the sensor data based on the signal dynamics.

* * * * *